(12) United States Patent
Kheiri et al.

(10) Patent No.: US 6,364,889 B1
(45) Date of Patent: *Apr. 2, 2002

(54) ELECTRONIC LANCING DEVICE

(75) Inventors: Mohammad A. Kheiri, Elkhart; Joseph E. Ruggiero, Goshen; Gary H. Bernstein, Granger, all of IN (US)

(73) Assignee: Bayer Corporation, Elkhart, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/441,970

(22) Filed: Nov. 17, 1999

(51) Int. Cl.⁷ .............................................. A61B 17/14
(52) U.S. Cl. ...................................... 606/181; 606/182
(58) Field of Search ................................ 606/182, 186, 606/185, 181, 169, 583, 156

(56) References Cited

U.S. PATENT DOCUMENTS

| | | | | |
|---|---|---|---|---|
| 2,714,890 A | * | 8/1955 | Vang | 606/169 |
| 3,086,288 A | * | 4/1963 | Balamuth et al. | 30/272 |
| 3,208,452 A | | 9/1965 | Stern | |
| 3,673,475 A | * | 6/1972 | Britton | 318/122 |
| 3,832,776 A | * | 9/1974 | Sawyer | 606/169 |
| 4,154,228 A | * | 5/1979 | Feldstein et al. | |
| 4,203,446 A | | 5/1980 | Höfert et al. | |
| 4,449,529 A | | 5/1984 | Burns et al. | |
| 4,462,405 A | | 7/1984 | Ehrlich | |
| 4,653,513 A | | 3/1987 | Dombrowski | |
| 5,029,583 A | | 7/1991 | Meserol et al. | |
| 5,188,118 A | | 2/1993 | Terwilliger | |
| 5,368,047 A | | 11/1994 | Suzuki et al. | |

* cited by examiner

Primary Examiner—Michael H. Thaler
(74) Attorney, Agent, or Firm—Jerome L. Jeffers (57) ABSTRACT

It has been discovered that the use of a substantially free-standing voice coil within a lancing device in coordination and combination with a stationary magnet and electronic circuit renders a much improved lancing device. The minimal weight of the free standing voice coil and the attractive forces of the magnet allow the battery-powered electronic circuit to maintain excellent control over the advancement and retraction of a lancet. When the electronic lancing device is initiated by a user, the voltage source within the electronic lancing device provides sufficient current through the voice coil such that the coil and lancet are repulsed from the magnet and propelled into the puncture site. The voltage source subsequently reverses the current through the voice coil to supply sufficient attractive current through the voice coil such that the dwell time of the lancet is minimized and the lancet is retracted from the puncture site and pulled toward the magnet within the housing of the electronic lancing device.

14 Claims, 8 Drawing Sheets

ELECTRONIC LANCING DEVICE

TECHNICAL FIELD OF INVENTION

The present invention relates generally to an electronic lancing device. More particularly, the present invention relates to an electronic lancing device comprising an electronic circuit that controls the movement of the lancet, mounted on a floating voice coil (bobbin) over a stationary magnet in a metal housing.

BACKGROUND OF THE INVENTION

Lancing devices are used for obtaining a body fluid such as capillary blood or interstitial fluid from various body sites. A typical user of a mechanical lancing device is a person in a program of self-blood glucose monitoring for treatment of diabetes. Generally, the user depresses a firing button on a lancing device at a selected puncture site to activate the lancing device to puncture the skin at the site. Once the skin has been punctured and the lancet retracts from the lancing site, a small amount of body fluid such as capillary blood or interstitial fluid forms on the skin at the puncture. The drop of body fluid on the surface of the skin at the puncture site is then applied to a test sensor.

A major problem many existing mechanical lancing devices face is the amount of pain experienced by the user of the device. Three significant reasons related to the lancing devices contribute to an increased amount of user pain. The lancets in many lancing devices undergo side-to-side vibration while moving to puncture the skin. This vibration can lead to an irregular puncture, causing unnecessary pain and discomfort to a user.

Another reason contributing to increased user pain associated with existing mechanical lancing devices is the repeated bouncing into and out of the skin that occurs upon insertion of the lancet into the puncture or lancing site. Typical mechanical lancing devices have been shown to penetrate the skin two to six times before the lancet stops oscillating.

A further reason for elevated user pain is the relatively slow speed at which the lancet travels into and from the skin and the period of time that the lancet remains inside the skin or "dwell time." A slower speed of lancet puncture, a longer duration of dwell time inside the skin, and a slower speed of lancet retraction all augment the amount of pain that a user experiences.

Accordingly, there exists a need for a lancing device that reduces user pain by eliminating the lancet from bouncing into and out of the skin, eliminating or reducing the vibration of the lancet when fired into the puncture site, and increasing the speed at which the lancet enters in and retracts from the skin, and controlling the dwell time of the lancet inside the skin.

SUMMARY OF THE INVENTION

The present invention provides an electronic lancing device comprising a stationary magnet mounted in a metal shell. A free-floating bobbin with attached coil is disposed over the magnet. The reciprocating movement of the bobbin's forward, reverse and dwell positions are precisely controlled by an electronic circuit.

It has been discovered that the use of a substantially free-standing voice coil within a lancing device in coordination and combination with a stationary magnet and electronic circuit renders a much improved lancing device. The minimal weight of the free standing voice coil and the attractive forces of the magnet allow the electronic circuit to maintain excellent control over the advancement and retraction of a lancet. When the electronic lancing device is initiated by a user, the electronic circuit within the electronic lancing device provides sufficient current through the voice coil such that the coil, bobbin and lancet are repulsed from the magnet and propelled into the puncture site. The electronic circuit subsequently reverses the current to supply sufficient attractive current through the voice coil such that the lancet is retracted from the puncture site and pulled toward the magnet within the housing of the electronic lancing device. The electronic circuit can also control the pause or dwell time between the advancement and the retraction of the bobbin and lancet.

BRIEF DESCRIPTION OF THE DRAWINGS

Other objects and advantages of the invention will become apparent upon reading the following detailed description and upon reference to the drawings in which.

While this invention is satisfied by embodiments in many different forms, there is shown in the drawings and will herein be described in detail preferred embodiments of the invention. It is understood that the present disclosure is to be considered as exemplary of the principles of this invention and is not intended to limit the invention to the embodiments illustrated. The scope of the invention will be measured by the appended claims and their equivalents.

DESCRIPTION OF ILLUSTRATIVE EMBODIMENTS

Figure 1:
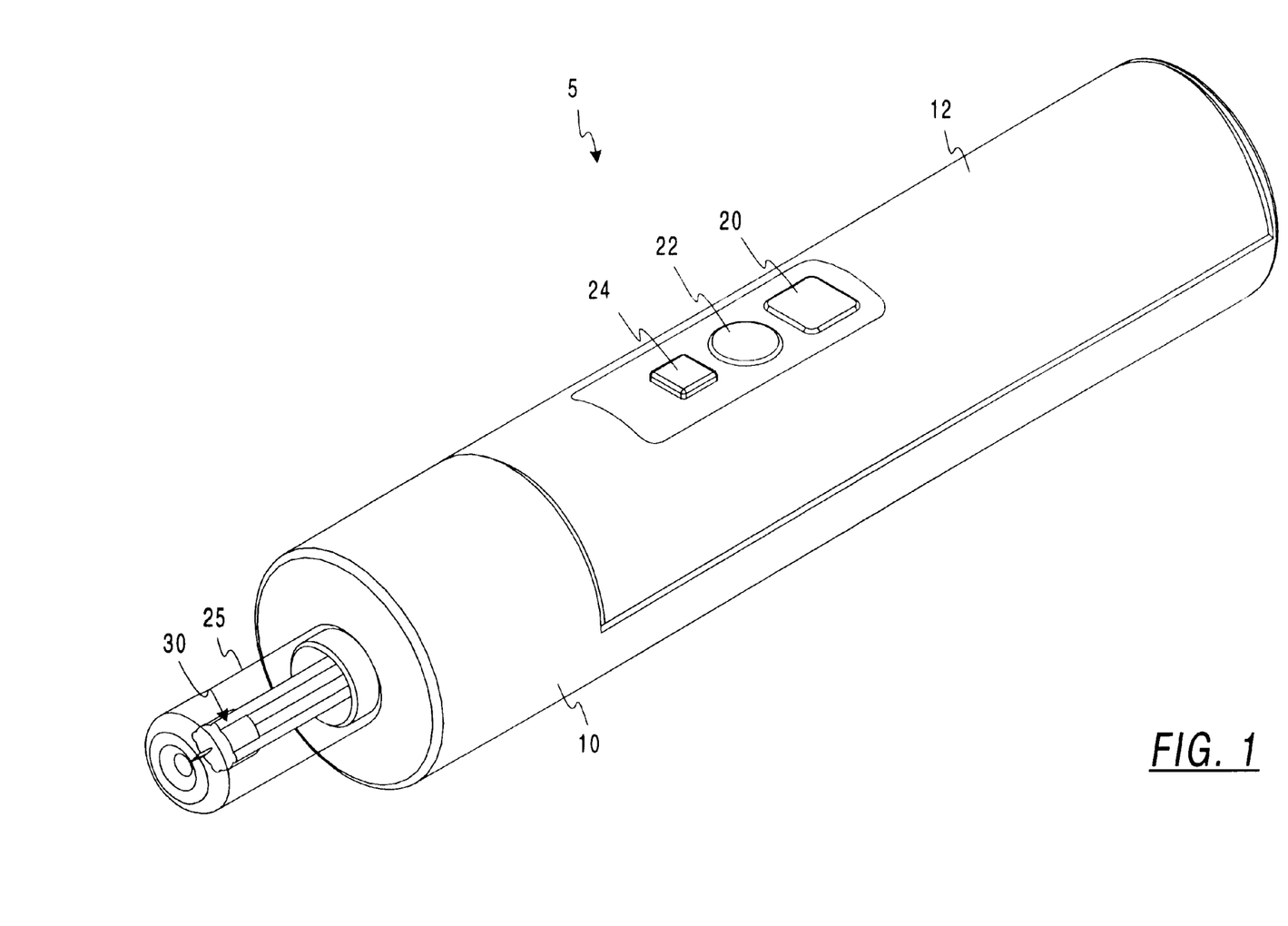
FIG. 1 is an assembly view of the retracted position of one embodiment of the electronic lancing device.

The electronic lancing device of the present invention is generally designated by the reference number 5 in the drawings. The electronic lancing device 5 shown in FIG. 1 is a handheld cylindrical stand-alone model. The lancing device 5, however, can also be an integral component of a blood test sensor. An electronic lancing device 5 can take on many shapes such as rectangular, square and oval. According to one embodiment of the present invention, the electronic lancing device 5 as shown in FIG. 1 comprises a housing 10, a cover 12, a power button 20, a firing button 22, a LED display 24, an end cap 25, and a lancet 30. As shown in FIG. 1, the housing 10 is manufactured from a plastic or similar material and comprises a cylinder-shaped housing 10 that allows access to the electronic circuit and other items located within the electronic lancing device 5. The cylindrical housing 10 has one closed end and one partially closed end. The cover 12 envelops the portion of the housing 10 that allows access to the internal electronic circuit. The cover 12 also comprises control signals such as the power button 20, the firing button 22 and the LED display 24. The power button 20 is a relatively small article that protrudes from one external wall of the cover 12 in accordance with one embodiment of the present invention. In order to operate the electronic lancing device 5, a user activates the electronic lancing device by depressing the power button 20. It is also contemplated in accordance with the present invention that the power button 20 could be disposed on one end of the electronic lancing device 5. It is further contemplated in accordance with the present invention that the power button 20 protrudes from an external surface of the housing 10. It is further contemplated that the power button 20 could be circular, square, rectangular, or any other shape that would facilitate simple firing of the firing button 22.

After the power button 20 is depressed and the electronic lancing device 5 is aligned against the puncture site, the user depresses the firing button 22 to initiate the lancing process. The firing button 22 is another relatively small article that protrudes from the cover 12 and is disposed adjacent the power button 20. In order for visually impaired users to operate the electronic lancing device 5, the firing button 22 embodying the present invention possesses at least one external feature that distinguishes it from the power button 20. It is contemplated in accordance with the present invention that the firing button 22 can be circular and the power button 20 can be rectangular, as shown in FIG. 1. It is also contemplated that the power button 20 and the firing button 22 can be hexagonal, pentagonal, or other shapes. It is further contemplated that the surface of either the power button 20 or the firing button 22 can be imprinted with other distinguishing features, for example, a dimple or a pimple, in order to distinguish from the other button. It is also contemplated in accordance with the present invention that the firing button 22 may protrude from an external surface of the housing 10.

Before depressing the firing button 22, the color exhibited by the LED display 24 notifies the user if the lancing device 5 is operable. The optional LED display 24 can be disposed adjacent the firing button 22 on the cover 12. For example, the LED display 24 may exhibit a red light if the electronic lancing device 5 is not prepared for operation and a green light if the electronic lancing device 5 is prepared for operation. It is contemplated in accordance with one embodiment of the present invention that the LED display 24 can exhibit alternative colors to indicate if the electronic lancing device can be operated.

As shown in FIG. 1, the end cap 25 is a cylindrical plastic article with openings at each end. The lancet 30 is a narrow sharply pointed object removably attached to a bobbin and designed to penetrate human skin. The end cap 25 serves both to protect the lancet 30 from damage and to protect the user from inadvertent contact with the sharply pointed lancet 30. Additionally, the end cap 25 is replaceable to protect multiple users and to control the depth of puncture. FIG. 1 depicts the lancet 30 being fully disposed within the end cap 25, referred to as the "retracted position." After the user depresses the firing button 22, the lancet advances from within the end cap to the piercing site to pierce the skin. The lancet is referred to as being in the "activated position" when it has advanced from within the end cap into the piercing site, as further described below.

Figure 2:
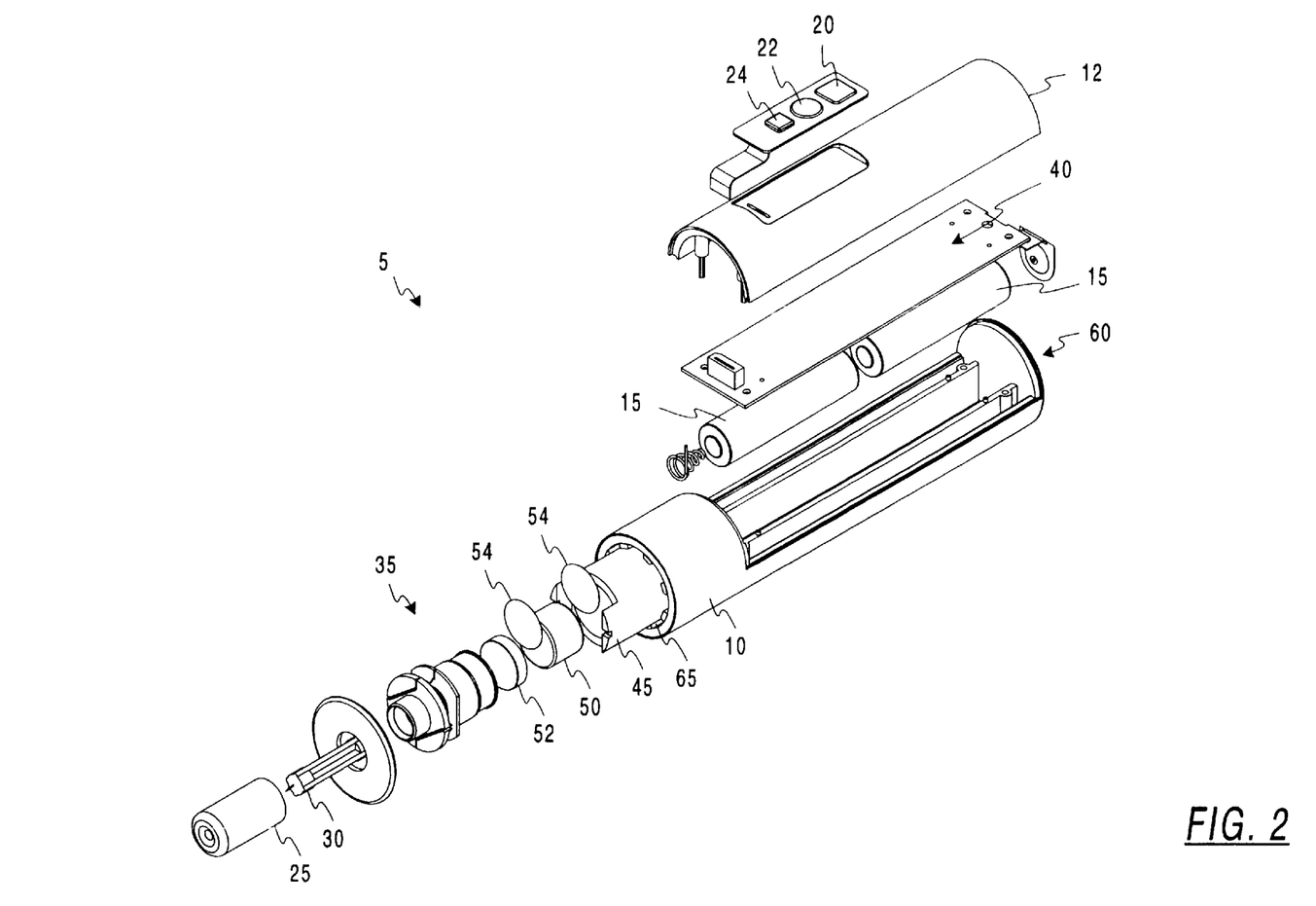
FIG. 2 is an exploded view of an electronic lancing device embodying the present invention.

A user selects and prepares a puncture or lancing site in the finger or other site, removes the end cap 25 to insert a lancet 30 into one end of the bobbin 35 (FIG. 2). The user then replaces the end cap 25 and presses the end cap 25 against the skin at the selected puncture or lancing site. After activating the electronic lancing device 5 with the power button 20 and ensuring that the light exhibited by the LED display 24 indicates that the electronic lancing device is operable, the user initiates the lancing process by depressing the firing button 22. The electronic lancing device 5 is then removed from the puncture or lancing site to reveal a body fluid such as capillary blood or interstitial fluid. The fluid can be then touched or put into contact with a blood or interstitial fluid test sensor where the desired tests are performed. The user can then remove the end cap 25 and lancet 30 from the electronic lancing device 5.

FIG. 2 depicts an exploded view of the electronic lancing device 5 of one embodiment of the present invention. The electronic lancing device 5 comprises a housing 10, a cover 12, batteries 15, a power button 20, a firing button 22, a LED display 24, an end cap 25, a lancet 30, a bobbin 35, a steel shell 45, a magnet 50, a steel block 52 and adhesive 54.

The housing 10 comprises a generally tubular body member with a cover 12 and two ends, a closed rear end 60 and an open front end 65. The housing 10 protects and provides an outer casing for the internal components of the electronic lancing device 5. In one embodiment of the housing 10, the housing is made of a suitable plastic material. A voltage source such as one or more batteries 15 is connected to an electronic circuit 40. The electronic lancing device 5 as shown in FIG. 2 comprises two AAA-size batteries. It is contemplated that 9 Volt or AA-size, AAAA-size, N cell, coin or any other suitable type of battery could be used within the electronic lancing device 5. It is also contemplated in accordance with the present invention that the electronic lancing device 5 could use a rechargeable battery. In order to effectuate an adequate advancement and retraction of the lancet into and out of the skin, the battery 15 carries a suitable voltage and current generating capabilities. The open front end 65 of the housing 10 provides a means for the inward and outward movement of the lancet 30 and bobbin 35 during operation of the electronic lancing device 5.

The firing button 22 initiates the sequence by which the lancet is propelled into the puncture site and retracted therefrom out of the puncture site. After the firing button 22 is depressed, the timing chip of the in-stroke and control circuitry, as described below, creates sufficient current to enable the bobbin 35 and the removably-attached lancet 30 to advance from their initial position into the puncture or lancing site. The out-stroke creates sufficient repulsive magnetic field to force the lancet and bobbin 35 away from its initial "retracted" position and into the "activated position." As used herein, the lancet 30 is in its retracted position when it is fully within the end cap 25 and in its activated position when it is fully extended away from the magnet 50. At its activated position, the electronic lancing device has completed the out-stroke and the lancet is fully inserted into the puncture site. In order to initiate the out-stroke, the firing button 22 is connected to at least one wire leading to the electronic circuit 40.

After the out-stroke creates sufficient repulsive charge to force the lancet 30 from its initial position within the end cap 25 away from the magnet 50 and into the puncture site, another timer circuit, as detailed below, initiates an in-stroke. The timing circuit of the in-stroke reverses the current, creating enough attractive force to retract the lancet 30 from the skin and return the bobbin 35 and the lancet 30 to the retracted position within the end cap 25. One embodiment of the present invention allows the user to initiate the lancing process only when a lancet 30 has been inserted into the bobbin 35.

Figure 3:
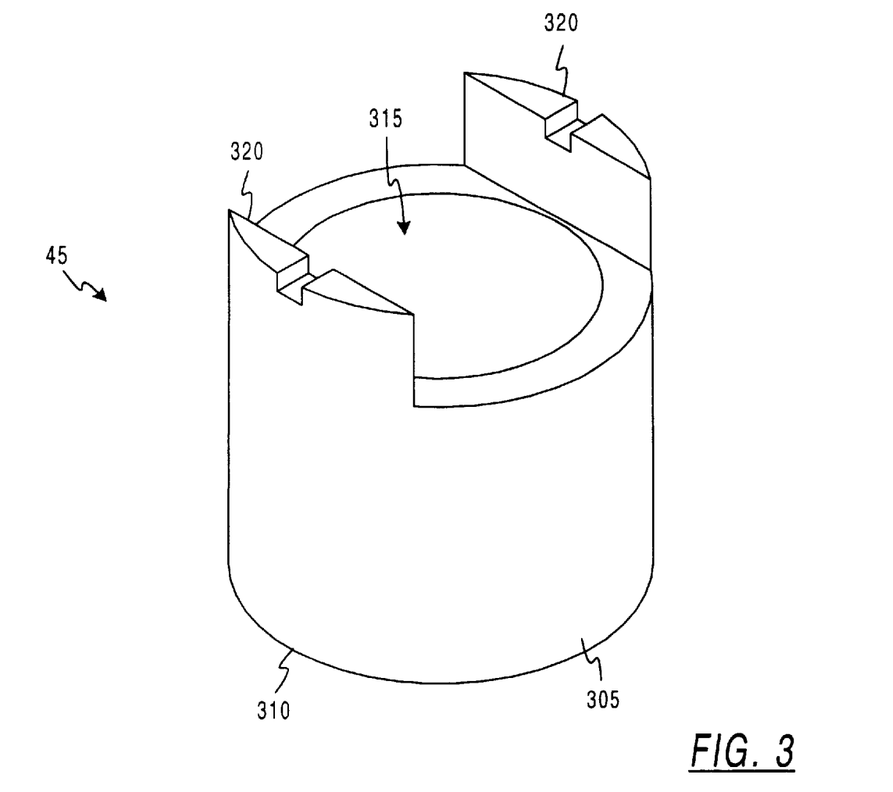
FIG. 3 is an isometric view of the steel shell of one embodiment of the present invention.

As shown in FIG. 2 and detailed in FIG. 3, a steel shell 45 comprises a generally tubular body member 305 with a closed end 310, an open end 315 and guide arms 320. The steel shell 45, disposed within the housing 10, serves to house the magnet 50 and a steel block 52. The steel shell further provides partial housing for the bobbin 35. During operation of the electronic lancing device 5, the steel shell 45 proscribes the path of motion of the free moving bobbin 35 during both the out-stroke and in-stroke. Extending beyond the open end 315 of the steel shell 45 is at least one guide arm 320. The guide arms 320 allow for only one directional translation motion. It is preferable that there are at least two guide arms 320. During the out-stroke of the electronic lancing device 5, the bobbin 35 is expelled out of the steel shell 45 and toward the lancing site. The in-stroke provides sufficient attractive force to attract the bobbin 35 into the steel shell 45. The duration of the end stroke is sufficient to prevent bouncing of the bobbin 35, thus preventing multiple punctures.

The open end 315 of the steel shell 45 is directed toward the open end 65 of the housing 10. The open end 315 of the steel shell 45 provides an opening large enough for the magnet 50 and the steel block 52 to be inserted into the steel shell 45. The open end 315 also provides sufficient opening for the bobbin 35 to be partially inserted into the steel shell 45.

Figure 4:
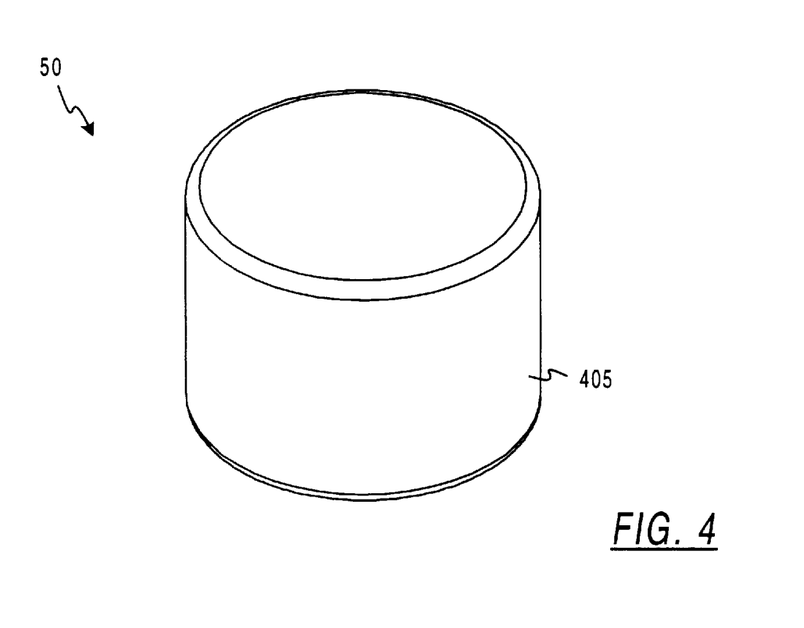
FIG. 4 is an isometric view of the magnet of one embodiment of the present invention.

A magnet 50 is mounted within the steel shell 45. The magnet 50 is coaxially centered and mounted inside the steel shell 45, within the housing 10. As shown in FIG. 4, the magnet 50 comprises a solid, generally cylindrical body member 405 that fits within the steel shell 45. As shown in FIG. 2, an adhesive 54 is placed on both the top surface and bottom surface of the magnet 50. It is contemplated in accordance with the present invention that the adhesive 54 is a contact layer containing adhering materials on both sides. The adhesive 54 on the bottom surface of the magnet 50 will attach the bottom surface of the magnet 50 to the steel shell 45. The adhesive 54 on the top surface of the magnet 50 will attach the top surface to a steel block 52.

Figure 5:
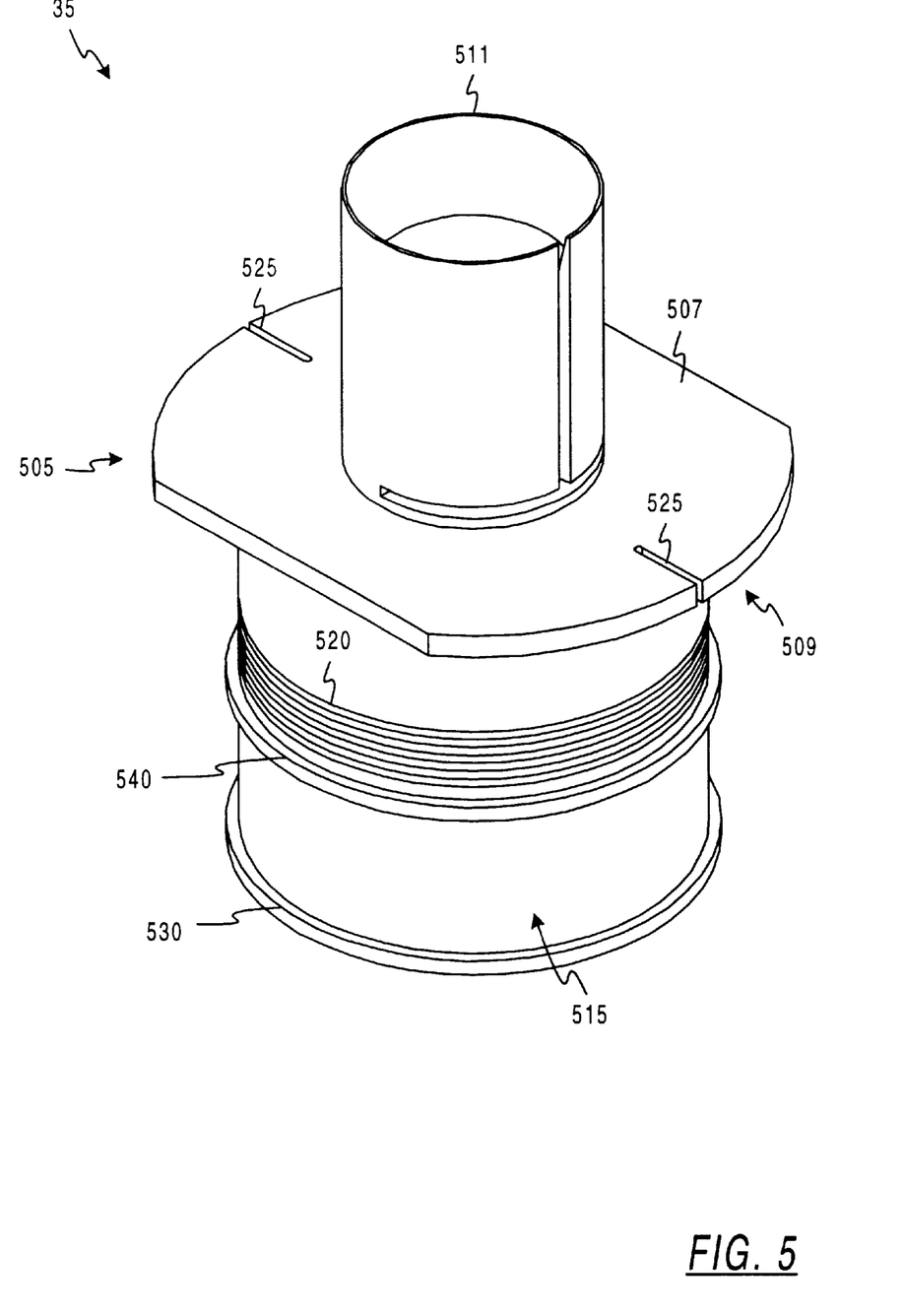
FIG. 5 is an isometric view of the bobbin of one embodiment of the present invention.

As shown in FIG. 5, a bobbin 35 comprises a flat disc 505, a first surface 507, a second surface 509, a first generally tubular body member 511, and a second generally tubular body member 515. The generally tubular body member 511 is located and attached to the first surface 507 of the flat disc 505. A second generally tubular body member 515 is located and attached to the second surface 509 of the flat disc 505.

Figure 6:
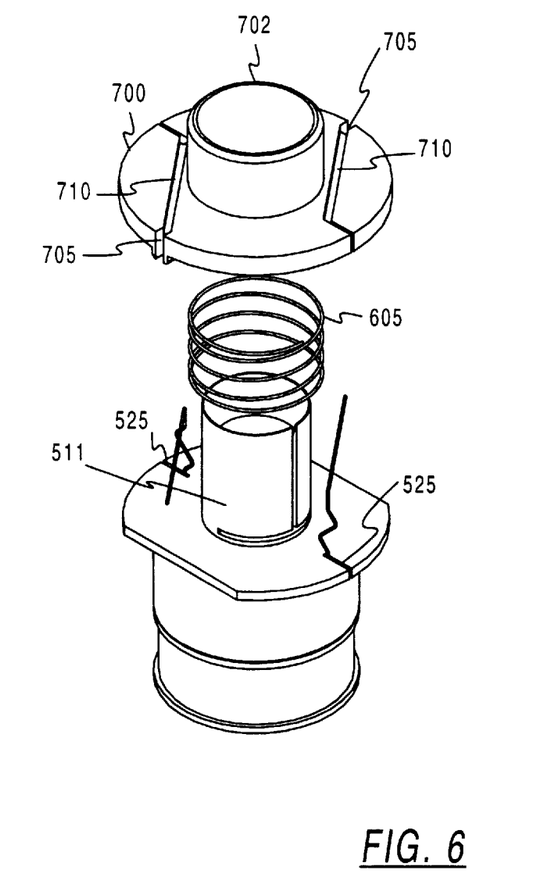
FIG. 6 is an exploded view of bobbin-coil-cap assembly of one embodiment of the present invention.

At least a portion of the second generally tubular body member 515 is wrapped by a coil of wire 520 (e.g., 33-gauge wire) winding in one or more layers. It is contemplated in accordance with the present invention that the wire 520 may encircle all or a portion of the length of the second tubular body member 515. Furthermore, as shown in FIG. 6, the two ends of the coil of wire 520 extend through a slot 525 in the flat disc 505. Contact adhesive is applied to the wire 520 to retain its place around the second generally tubular body member 515. Ribs 530 and 540 are higher than the layers of coil 520 in order to protect the coil of wire 520 from rubbing during operation. The two timer chips and control circuit, as described below, direct the current through the wire, creating enough repulsive forces to expel the bobbin 35 and the lancet 30 from their retracted positions toward the lancing site and attract it back to the retracted position.

Figure 7:
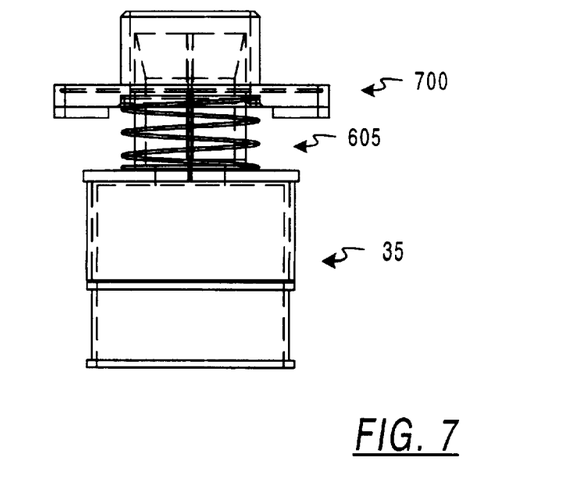
FIG. 7 is an assembled view of bobbin-coil-cap assembly of one embodiment of the present invention.

Further comprising the bobbin 35 is a first generally tubular body member 511 attached to the first surface 507, as shown in FIG. 6. The fixed cap 700 is attached to the housing 10 and contains a hollow tubular section 702 centrally located to enable the cap 700 to fit over the top of the first generally tubular body member 511. A slot 705 exists on both sides of the cap 700. The wires that extend from the slots 525 of the disc 505 are attached through the slots 705 into channels 710 of the cap 700. The wires are connected from the channels 710 to the electronic circuit 40. A compression spring 605 is located between the cap 700 and the disc 505. As current flows through the wire 520, the bobbin 35 and lancet 30 extend towards the puncture site. Upon retraction, the lancet 30 and bobbin 35 return to the original retracted position. The purpose of compression spring 605 is to maintain the retracted position of the bobbin 35 when not energized. FIG. 7 shows a front view of the bobbin-coil-cap assembly of one embodiment of the present invention.

Figure 8:
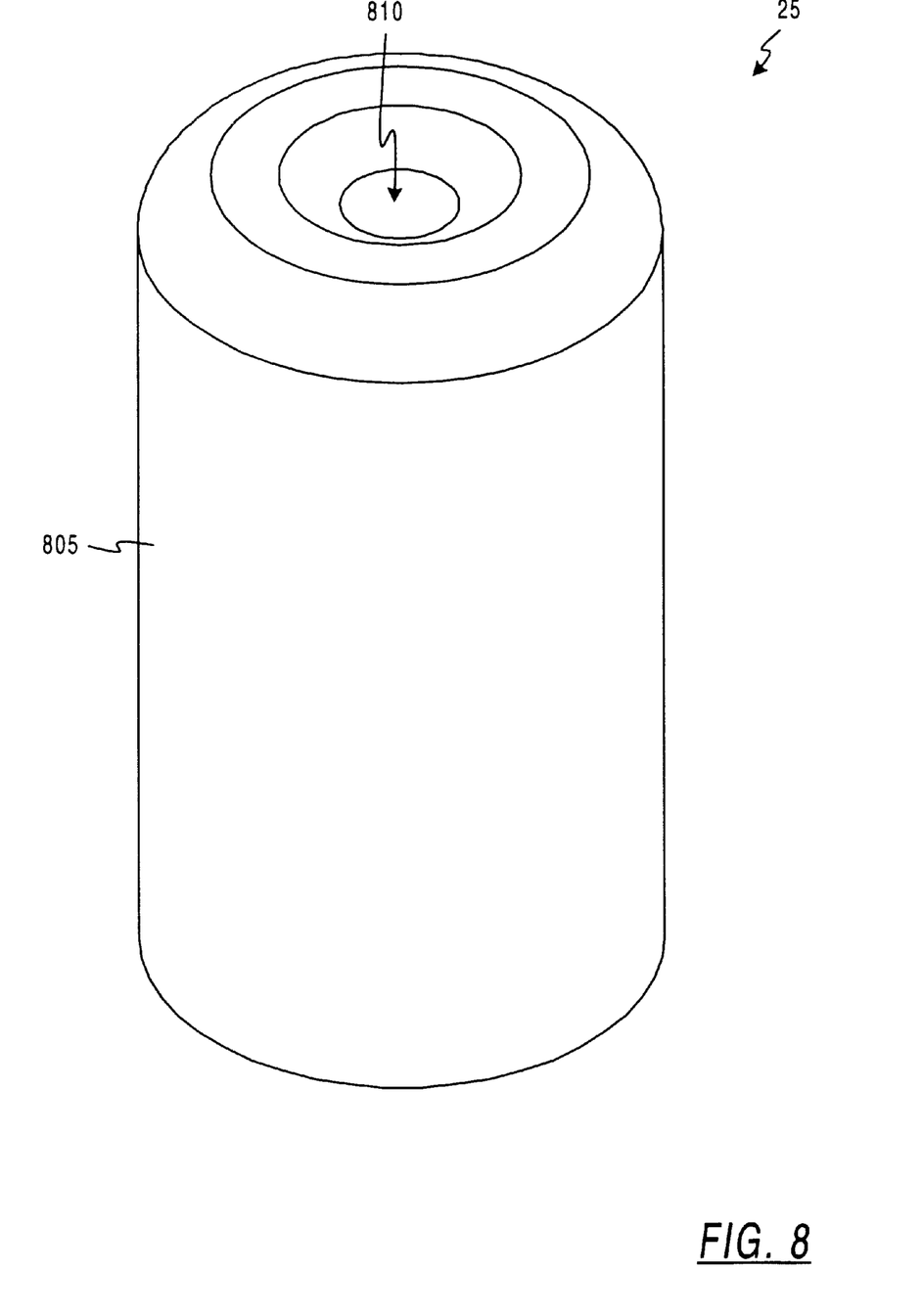
FIG. 8 is an isometric view of the end cap of one embodiment of the present invention.

A removable end cap 25 can be attached to the tubular body member 702. As shown in FIG. 8, the end cap 25 consists of a generally tubular body member 805 with an open end and a partially closed end. The open end of the end cap 25 is designed to be attached to the tubular body member 702 of the cap 700. The inner diameter of the end cap 25 at the open end is larger than the outer diameter of the tubular body member 702 to allow the end cap 25 to fit over the tubular body member 702. The outer diameter of tubular member 511 is less than the inner diameter of this tubular body member 702. The partially closed end of the end cap 25 contains an opening 810 that allows the tip of the lancet 30 to pass through. Prior to and post operation, the lancet is safely housed within the end cap 25.

Since the present invention can be satisfied by embodiments in many different forms, it is contemplated in accordance with the present invention that the electronic lancing device 5 can take on a cubic shape instead of a generally tubular shape. Similarly, each of the items previously referred to possess a generally tubular shape might have a generally cubic shape, with a square or rectangular shape. Furthermore, it is also contemplated in accordance with the present invention that other shapes exist that will enable this invention.

Figure 9:
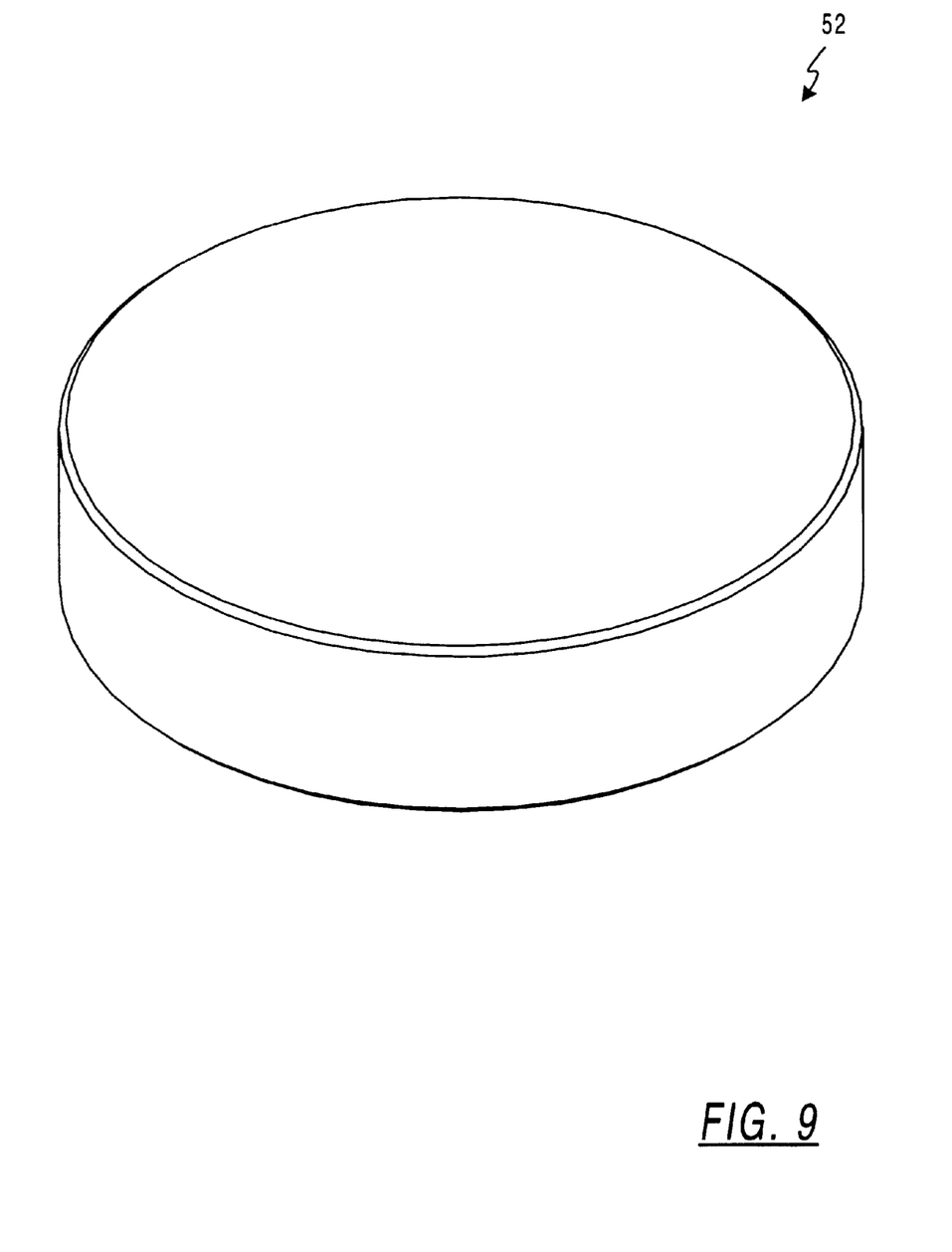
FIG. 9 is an isometric view of the steel block of one embodiment of the present invention.

As generally shown in FIG. 2 and further shown by FIG. 9, a steel block 52 is coaxially centered and mounted on top of the magnet 50. The steel block 52 brings the majority of the magnetic flux lines to intersect the coils in order for the electronic lancing device to achieve maximum efficiency. The steel block 52 may be a solid generally cylindrical disc formed from steel. Magnetic flux lines return to the magnet through the steel shell 45.

Figure 10:
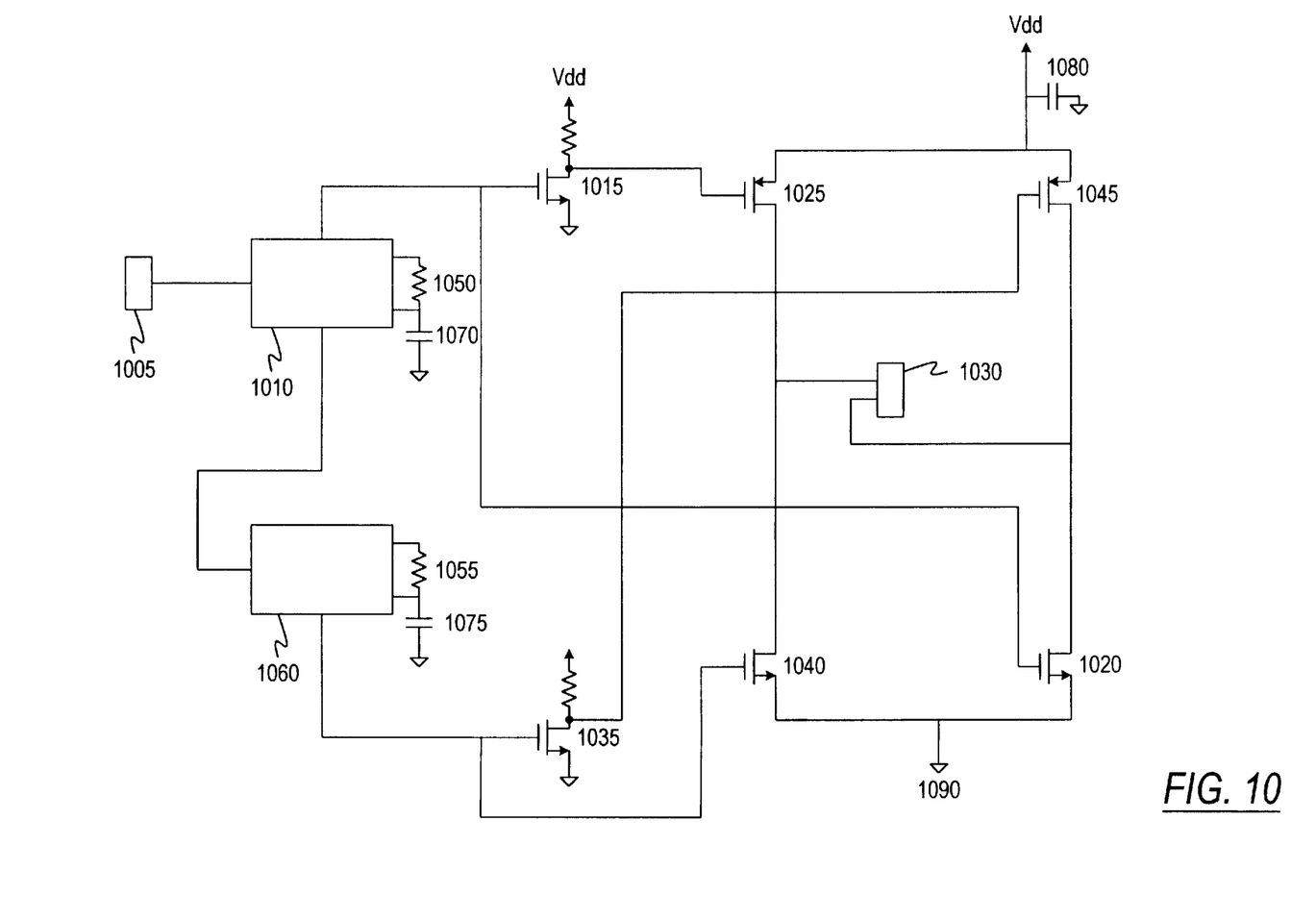
FIG. 10 is a schematic view of an electronic circuit of one embodiment of the present invention.

The electronic circuit 40 of the present invention could be designed in a variety of ways. For example, the electronic circuit of FIG. 10 comprises a switch 1005, two timing chips 1010 and 1060, several resistors and at least two transistors. When the user depresses the firing button 22, the switch 1005, as shown in FIG. 10, of the electronic circuit 40 forces a falling edge transition at the trigger of pin 2 of a TLC555-timing chip 1010. The timing chip 1010 regulates the delivery of the bobbin and lancet. The timing chip 1010 triggers the out-stroke during which the lancet is advanced into the puncture or lancing site. It is preferable that the duration of the out-stroke is adjustable, being generally less than about 7 milliseconds. It is more preferable that the duration of the out-stroke is as short as possible. Transistors 1015, 1035, 1040 and 1020 are of the n-channel variety, so they are "on", or conduct current, when their gate voltages are at a high voltage relative to the voltage source, Vdd, and do not conduct current when their gate voltages are at a low voltage. Transistors 1025 and 1045 are of the p-channel variety, so they are "on" or conduct current when their gate voltages are at a low voltage relative to the voltage source, Vdd, and do not conduct current when their gate voltages are at a high voltage. The timing chip 1010 controls the voltage at the gates of a level-shifter transistor 1015 and transistor 1020. When the voltage at these gates increases (hereinafter referred to as "goes high"), transistors 1015 and 1020 turn on, and simultaneously the gate of transistor 1025 decreases, or "goes low", so transistor 1025 turns on. During this time, the gates of transistors 1035 and 1040 are low, so these transistors are off, and the gate of transistor 1045 is high, so transistor 1045 is off. Therefore the current path through the coil 1030 is from Vdd through transistor 1025, through the coil 1030, and then 1020 to ground, 1090. The direction of this current through the coil causes a repulsive magnetic field in the coil 1030 that causes the voice coil 1030 and the bobbin 35 to be repulsed by the permanent magnet out of the steel shell 45, this action comprising the out-stroke. This magnetic field develops enough energy to allow the lancet to surge away from the magnet 50 and into the puncture or lancing site. The transistors 1020 and 1025 allow adequate current from the power source, Vdd, and charged capacitor 1080 during the delivery of the lancet and the bobbin into the puncture site.

After a time set by the resistor 1050 and the capacitor 1070, the timer 1010 times out, decreasing the voltage on the gates of transistors 1015 and 1020, and simultaneously, the falling edge transition of the out-stroke triggers pin 2 of a second TLC555-timing chip 1060. The timing chip 1060 regulates the retraction of the bobbin and lancet. The timing chip 1060 causes the gates of transistors 1035 and 1040 to go high, turning transistors 1035 and 1040 on, and simultaneously the gate of transistor 1045 goes low, so transistor 1045 turns on. During this time, the gates of transistors 1015 and 1020 are low, so these transistors are off, and the gate of transistor 1025 is high, so transistor 1025 is off. Therefore, the current path through the coil 1030 is from Vdd through transistor 1045, through the coil 1030, and then 1040 to ground, 1090. The direction of this current through the coil causes an attractive magnetic field in the coil 1030 which causes coil 1030 and the bobbin 35 to be attracted by the permanent magnet into the steel shell 45. This action comprises the in-stroke during which the lancet is removed or pulled from the puncture or lancing site. The transistors 1040 and 1045 allow adequate current from the power source, Vdd, and charged capacitor 1080 during the extraction of the lancet and the bobbin from the puncture site. After a time set by resistor 1055 and capacitor 1075, the timer 1060 times out, leaving the bobbin in the retracted position, held by the spring 605. The in-stroke is of sufficient duration so as to eliminate bouncing of the bobbin, resulting in reduced pain to the user. The duration of the in-stroke is from about 10 to about 15 milliseconds.

While the present invention has been described with reference to the particular embodiments illustrated, those skilled in the art will recognize that many changes and variations may be made thereto without departing from the spirit and scope of the present invention. The embodiments and obvious variations thereof are contemplated as falling within the scope and spirit of the claimed invention, which is set forth in the following

What is claimed is:

1. An electronic lancing device comprising:
   a housing;
   a hollow, cylindrical-shaped shell having at least one guide arm, said shell being fixedly mounted within the housing;
   a magnet fixedly mounted in said shell;
   a bobbin being partially disposed in said rigid shell for reciprocating movement therein, said bobbin being moveable from a retracted position to an activated position and from the activated position to the retracted position, said bobbin being constrained to one directional translation motion by said at least one guide arm of said shell when moving from the retracted position to the activated position and from the activated position to the retracted position;
   a coil having at least one winding disposed around said bobbin, said coil being attached to said bobbin;
   a lancet removably attached to said bobbin; and
   an electronic circuit electrically coupled to said coil for controlling the movement of said bobbin, said electronic circuit supplying current in a first direction to said coil to create a repulsive magnetic field in the coil causing the coil and the bobbin to be repulsed by the magnetic for moving said bobbin from the retracted position to the activated position said electronic circuit supplying current in a second direction to said coil to create an attractive magnetic field in the coil causing the coil and the bobbin to be attracted by the magnetic for moving said bobbin from the activated position to the retracted position, said second directed being the reverse of said first direction.

2. The electronic lancing device of claim 1, wherein said housing further comprises a steel block to allow at least a majority of the magnetic flux lines to intersect said coil.

3. The electronic lancing device of claim 2, wherein said electronic circuit comprises at least one timer circuit, at least one wave-shaping amplifier circuit, at least one power transistor to provide current to the bobbin, and at least one capacitor to provide current to the bobbin.

4. The electronic lancing device of claim 2, wherein said electronic circuit comprises two timer circuits.

5. The electronic lancing device of claim 4, wherein one of said timer circuits regulates the delivery of said bobbin and said lancet.

6. The electronic lancing device of claim 5, wherein the duration of said delivery of said bobbin is less than about 7 milliseconds.

7. The electronic lancing device of claim 4, wherein one of said timer circuits regulates the retraction of said bobbin and said lancet.

8. The electronic lancing device of claim 7, wherein the duration of said retraction of said bobbin is from about 10 to about 15 milliseconds.

9. The electronic lancing device of claim 1 wherein said coil is a voice coil.

10. A method of delivering and retracting a lancet with an electronic lancing device including a hollow, cylindrical shaped shell having at least one guide arm fixedly mounted within a housing of the device, a magnet fixedly mounted in the housing, a bobbin being partially disposed in the shell for reciprocating movement therein, and a coil having a least one winding disposed around said bobbin, said coin being attached to said bobbin, the lancet being attached to said bobbin, said method comprising:
   supplying said coil with an electric current in a first direction;
   generating a magnetic field around said magnet resulting in sufficient repulsive forces between said magnet and said coil to move said lancet from a retracted position to an activated position;
   supplying said coil, with an electric current in a second direction, the second direction being the reverse of the first direction;

generating an attractive magnetic field around said magnet resulting in sufficient attractive forces between said magnet and said coil to move said lancet from the activated position to the retracted position; and constraining the movement of the bobbin to one direction translation motion with said at least one guide arm.

11. The method of delivering and retracting a set forth in claim 10, wherein said energizing includes initiating a power source including a battery and an electronic circuit.

12. The method of delivering and retracting a lancet set forth in claim 11, wherein said electronic circuit comprises at least one timer circuit, at least one wave-shaping amplifier circuit, at least one transistor to provide adequate current during said delivery and said retraction of said bobbin and said lancet.

13. The method of delivering and retracting a bobbin set forth in claim 11, wherein said electronic circuit comprises at least one capacitor.

14. The method of claim 10 wherein said coil is a voice coil.

* * * * *